United States Patent [19]

Thetford et al.

[11] Patent Number: 5,730,759
[45] Date of Patent: Mar. 24, 1998

[54] POLY-SUBSTITUTED PHTHALOCYANINES

[75] Inventors: Dean Thetford, Manchester; Peter Gregory, Bolton, both of England

[73] Assignee: Zeneca Limited, London, England

[21] Appl. No.: 548,171

[22] Filed: Oct. 25, 1995

Related U.S. Application Data

[62] Division of Ser. No. 344,682, Nov. 17, 1994, Pat. No. 5,486,274, which is a continuation of Ser. No. 777,719, Oct. 21, 1991, abandoned.

[30] Foreign Application Priority Data

| Nov. 2, 1990 | [GB] | United Kingdom | 9023894 |
| Nov. 21, 1990 | [GB] | United Kingdom | 9025280 |

[51] Int. Cl.$^6$ .................................................. D06L 3/04
[52] U.S. Cl. .................. 8/137; 8/142; 8/103; 8/107; 8/108.1; 8/110; 8/111; 8/115.52; 8/115.53; 8/661; 510/301
[58] Field of Search .................. 8/137, 142, 103, 8/107, 108.1, 110, 111, 115.52, 115.53, 661; 252/95, 104, 105, 542, 543; 510/301

[56] References Cited

U.S. PATENT DOCUMENTS

| H477 | 6/1988 | Burger et al. | 385/27 |
| 1,489,394 | 4/1924 | Moore | 222/461 |
| 2,276,918 | 3/1942 | Bienert et al. | 540/132 |
| 2,414,374 | 1/1947 | Haddock | 540/129 |
| 3,927,967 | 12/1975 | Speakman | 8/103 |
| 4,033,718 | 7/1977 | Holcombe et al. | 8/103 |
| 4,240,920 | 12/1980 | de Fugue . | |
| 4,255,273 | 3/1981 | Sakkab . | |
| 4,256,597 | 3/1981 | Sakkab . | |
| 4,256,598 | 3/1981 | Sakkab . | |
| 4,318,883 | 3/1982 | Polony et al. | 422/22 |
| 4,368,053 | 1/1983 | Eckhardt et al. | 8/102 |
| 4,394,125 | 7/1983 | Holzle et al. | 8/103 |
| 4,400,173 | 8/1983 | Bearan | 8/109 |
| 4,456,452 | 6/1984 | Holzle et al. | 8/103 |
| 4,530,924 | 7/1985 | Polony et al. | 514/191 |
| 4,648,992 | 3/1987 | Grof et al. | 540/124 |
| 4,657,554 | 4/1987 | Reinert et al. | 8/107 |
| 4,769,307 | 9/1988 | Ozawa et al. | 430/270 |
| 4,935,498 | 6/1990 | Sessler et al. | 534/15 |
| 4,946,762 | 8/1990 | Albert et al. | 430/270 |
| 4,990,280 | 2/1991 | Thorengaard et al. | 510/301 |
| 5,106,872 | 4/1992 | Adler et al. | 514/587 |
| 5,109,016 | 4/1992 | Dixon et al. | 514/410 |
| 5,162,509 | 11/1992 | Sessler et al. | 534/15 |
| 5,484,915 | 1/1996 | Gregory et al. | 540/131 |
| 5,486,274 | 1/1996 | Thetford et al. | 204/157.5 |

FOREIGN PATENT DOCUMENTS

| 0047716 | 3/1982 | European Pat. Off. . |
| 0153278 | 8/1985 | European Pat. Off. . |
| 0232427 | 8/1987 | European Pat. Off. . |
| 0272565 | 6/1988 | European Pat. Off. . |
| 866309 | 4/1941 | France . |
| 2252386 | 6/1975 | France . |
| 812261 | 9/1978 | Germany . |
| 63-137997 | 6/1988 | Japan . |

OTHER PUBLICATIONS

V.M. Parikh, "Absorption Spectroscopy of Organic Molecules," Philippines: Addison–Kleley Publishing Company, Inc. 1974, pp. 13–30. (Month Unknown).
Chemical Abstracts, vol. 102, No. 2, Jan. 1985, No. 8233y, Oliver et al, "Synthesis and characterization of 2,19,16, 23–tetrakis(3–pyridyloxy)phthalocyanine".
Chemical Abstracts, vol. 111, No. 16, Oct. 1989, No. 136017d, Kinoshita et al, "Ettra(alkoxyphenoxy) phthalocyanines".
Advanced Organ. Chemistry: Reactions, Mechanism, Structure, 3rd edition, pp. 20–205, (1985). (Month Unknown).

*Primary Examiner*—Alan Diamond
*Attorney, Agent, or Firm*—Cushman Darby & Cushman IP Group of Pillsbury Madison & Sutro LLP

[57] ABSTRACT

The use of substituted phthalocyaines for removing stains from fabrics which comprises treating the stained fabrics with an aqueous composition comprising a phthalocyanine in which at least one of the peripheral carbon atoms in the 1–16 position of the phthalocyanine nucleus ($M_kPc$) of Formula (1),

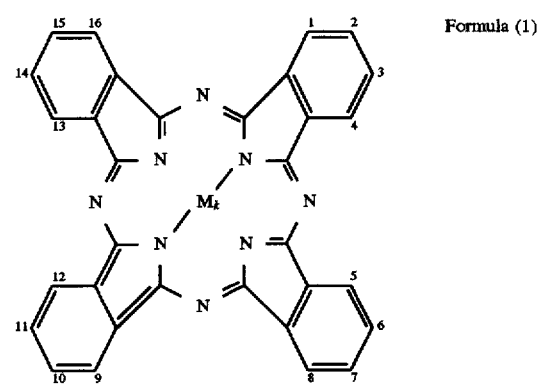

Formula (1)

wherein:
M is selected from H, metal, halometal, oxymetal and hydroxymetal; and
k is the inverse of ½ the valency of M;
is linked via an oxygen atom to an aromatic radical and the remaining peripheral carbon atoms are unsubstituted or substituted by any combination of atoms or groups and sulphonated derivatives thereof provided that the phthalocyanine absorbs electromagnetic radiation at a wavelength from 650 nm to 800 nm.

9 Claims, No Drawings

POLY-SUBSTITUTED PHTHALOCYANINES

This is a division of application Ser. No. 08/344,682, filed Nov. 17, 1994, now U.S. Pat. No. 5,486,274 which is a Continuation of appln. Ser. No. 07/777,719, filed Oct. 21, 1991 now abandoned.

This invention relates to the use of certain poly-substituted phthalocyanine compounds and certain sulphonated derivatives thereof to generate singlet oxygen, to the methods of preparing such compounds and to certain novel substituted phthalocyanines.

The present invention relates to the use of substituted phthalocyanines for the generation of singlet oxygen, in which at least one of the peripheral carbon atoms in the 1–16 positions of the phthalocyanine nucleus ($M_kPc$), as shown in Formula (1):

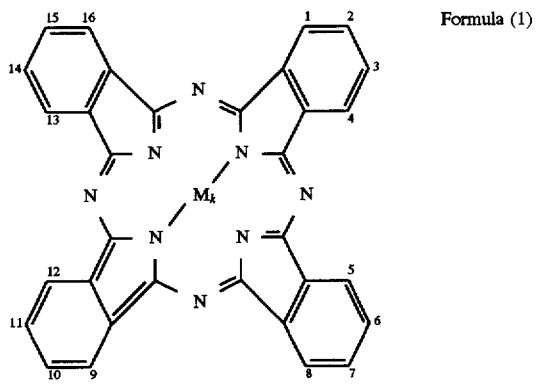

Formula (1)

wherein:

M is selected from H, metal, halometal, oxymetal and hydroxymetal; and k is the inverse of ½ of the valency of M; is linked via an oxygen atom to an organic radical, hereinafter referred to as pendant organic radical, the remaining peripheral carbon atoms being unsubstituted or substituted by any combination of atoms or groups and sulphonated derivatives thereof provided that the phthalocyanine absorbs electromagnetic radiation at a wavelength from 650 nm to 800 nm.

In the present phthalocyanines the phthalocyanine nucleus may be metal free or it may be complexed with a metal, an oxymetal group, a hydroxy metal group or a halometal group represented by M i.e. it may carry two hydrogen atoms at the centre of the nucleus or it may carry one or two metal atoms or oxymetal groups or hydroxy metal groups or halometal groups complexed within the centre of the nucleus. Preferred metals represented by M are those of Groups IA, IIA, IIIB, IVB, 1st, 2nd and 3rd transition rows and the lanthanide series of the Periodic Table.

Examples of suitable metals, halometal groups, hydroxy metal groups and oxymetal groups represented by M are Li, Na, K, Mg, ClAl, OHAl, Ca, ClSc, OHSc, Ni, Cu, Zn, ClGa, HOGa, OHRh, ClRh, ClIn, BrIn, OHIn, Sn, Ba, Ir, $SiCl_2$, SiO, $Si(OH)_2$, Pt, Pd, ClRu, OHRu, $Cl_2Ge$, $(OH)_2Ge$, P(V)$Cl_3$, P(III)Cl, POCl, $R^4Al$, $R^4Sc$, $R^4Gr$, $R^4Ga$, $R^4OAl$, $R^4OSc$, $R^4OCr$, $R^4OGa$, $R^4ORh$, $R^4Rh$, $R^4In$, $R^4OIn$, $R^4OSm$, $SiR^4_2$, $Si(OR^4_2)$, $R^4Ru$, $R^4ORu$, $R^4_2Ge$, $(R^4O)Ge$, $P(V)OR^4$, $P(III)OR^4$, $POR^4$ and $POOR^4$ in which $R^4$ is straight or branched chain $C_{1-12}$-alkyl, aryl or heteroaryl.

Where $R^4$ is alkyl it is preferably $C_{1-6}$-alkyl; where $R^4$ is aryl it is preferably selected from phenyl, benzyl, toluyl and 2-naphthyl and where $R^4$ is heteroaryl it is preferably pyridazyl or pyridyl.

In the present phthalocyanines it is preferred that M is Zn, ClAl, OHAl, ClRh, OHRh, ClIn, BrIn, OHIn, ClGa, OHGa, Pt, Pd, Li, Na, K, Ca, Ba, Mg, ClSc or OHSc, it is especially preferred that M is Zn, ClAl, OHAl, ClRh, OHRh, ClIn, BrIn, OHIn, ClGa, OHGa, Pt and Pd.

In the phthalocyanines used in the present invention each of the pendant organic radicals linked via oxygen to the phthalocyanine nucleus is independently selected from aromatic, heteroaromatic, aliphatic and alicyclic radicals, such that any one phthalocyanine nucleus may carry two or more different organic radicals.

It is preferred that each pendant organic radical is independently selected from mono- and bi-cyclic aromatic and heteroaromatic radicals.

Examples of suitable mono- and bi-cyclic aromatic and heteroaromatic radicals are phenyl, naphthyl, especially naphth-2-yl, pyridyl, thiophenyl, furanyl, quinolinyl, thiazolyl, benzothiazolyl and pyrimidyl each of which may be substituted.

Where the pendant organic radical is an aliphatic or alicyclic radical it is preferred that it is selected from $C_{1-20}$-alkyl especially $C_{1-10}$-alkyl; $C_{2-20}$-alkenyl especially $C_{3-10}$-alkenyl and $C_{4-8}$-cycloalkyl especially cyclohexyl, each of which may be substituted.

Optional substituents for the pendant organic radicals are preferably selected from $C_{1-20}$-alkyl, especially $C_{1-4}$-alkyl; $C_{1-20}$-alkoxy, especially $C_{1-4}$-alkoxy; $C_{1-20}$-alkenyl, especially $C_{2-4}$-alkenyl; $C_{1-20}$-alkylthio, especially $C_{1-4}$-alkylthio; $C_{1-20}$-alkoxycarbonyl, especially $C_{1-4}$-alkoxycarbonyl; hydroxy$C_{1-4}$-alkoxy; aryl, especially phenyl; $C_{1-4}$-alkylaryl, especially benzyl; arylthio, especially phenylthio; halogen, especially fluoro, chloro and bromo; —CN; —$NO_2$; —$CF_3$; —$COR^2$, —$COOR^2$, —$CONR^2R^3$—, —$SO_2R^2$, —$SO_2NR^2R^3$, —$NR^2R^3$ and —$OR^2$ in which $R^2$ and $R^3$ are independently selected from —H; alkyl, especially $C_{1-4}$-alkyl; aryl, especially phenyl; $C_{1-4}$-alkylaryl, especially benzyl and —$SO_3A$ in which A is H, or a metal or ammonium ion or substituted ammonium ion.

In the phthalocyanines used in the present invention it is preferred that from 4 to 16 of the peripheral carbon atoms are linked via an oxygen atom to a pendant organic radical and it is especially preferred that all 16 peripheral carbon atoms are linked via an oxygen atom to a pendant organic radical.

Examples of suitable atoms or groups which can be attached to any of the remaining peripheral carbon atoms of the phthalocyanine nucleus are hydrogen, halogen, sulphonate groups —$SO_3A$ in which A is H, or a metal or ammonium ion or a substituted ammonium ion, and any of the pendant organic radicals described above and hereinafter represented by R. It is preferred that the atoms or groups attached to the remaining peripheral carbon atoms are selected from —H, —F, —Cl, —Br, —I, —$SO_3H$, —$SO_3Na$, —$SO_3K$, —$SO_3Li$, and —$SO_3NH_4$ or any combination thereof. It is especially preferred that these atoms or groups are —H, —Cl, —Br, —$SO_3H$, —$SO_3Na$ or —$SO_3NH_4$.

The sulphonated derivatives of the phthalocyanines used in the present invention carrying up to 50 $SO_3A$ groups, preferably up to 40 $SO_3A$ groups and more preferably up to 30 $SO_3A$ groups, which are attached directly to the phthalocyanine nucleus and/or to the pendant organic radicals are a preferred group of compounds for the present invention.

In the preferred group the average number of $SO_3A$ groups is preferably from 2 to 40 and more preferably from 2 to 30 and especially preferably 16 to 30. It is also preferred that for each pendant organic radical there is at least one $SO_3A$ group, although each organic radical may carry none, one or more than one $SO_3A$ group.

Where A is a metal ion it is preferably an alkali or alkaline earth metal ion, especially an alkali metal ion such as a sodium, potassium or lithium ion. Where A is an ammonium ion it is preferably $^+NH_4$ or a substituted ammonium ion which enhances the water-solubility of the compound or a substituted ammonium ion of the formula $^+NQ_4$ which enhances the alcohol solubility of the compound. Examples of suitable substituted ammonium ions which enhance the water solubility of the compound are mono, di, tri and tetra alkyl and hydroxyalkyl ammonium ions in which the alkyl groups preferably contain from 1 to 4 carbon atoms such as $^+N(CH_3)_4$; $^+N(C_2H_5)_4$; $^+N(C_2H_4OH)_4$; $^+NH_3CH_3$; $^+NH_2(CH_3)_2$ and $^+NH(CH_3)_3$.

In the substituted ammonium ion of the formula $NQ_4$ at least one Q is a fatty aliphatic group and any remaining Q groups are $C_{1-4}$-alkyl or H. The fatty aliphatic group represented by Q preferably contains from 4 to 16, more preferably from 7 to 12 and especially preferably 7 to 9 carbon atoms. Preferred fatty aliphatic groups are alkyl and alkenyl groups which have straight- or branched-chains. Preferred alkyl groups, represented by Q, containing 8 or 9 carbon atoms are, 3,5,5-trimethyl- hexyl, 1,1,3,3-tetramethylbutyl and 2-ethylhexyl. Examples of other aliphatic chains are 1-ethyl-3-methylpentyl, 1,5-dimethylhexyl, 1-methylheptyl, 1,4-dimethylheptyl, 1,2,2-trimethylpropyl, 2-ethylbutyl, 1-propylbutyl, 1,2-dimethylbutyl, 2-methylpentyl, 1-ethylpentyl, 1,4-dimethylpentyl, 1-methylhexyl, 3-methylhexyl, 1,3,3-trimethylbutyl, 1-methylnonyl. The substituted ammonium ion represented by A preferably has one fatty alkyl group as described above, the remaining groups being preferably H or $C_{1-4}$-alkyl, especially H or methyl. Suitable ammonium ions include 2-ethylhexylammonium, 1,1,3,3-tetramethylbutylammonium and 3,5,5-trimethylhexylammonium.

In compounds of the Formula (1) each of the peripheral carbon atoms in the 1 to 16 positions of the phthalocyanine nucleus are attached to a group Y and each Y is independently selected from —H, halogen, —$SO_3A$ in which A is as hereinbefore defined, and OR in which R is a pendant organic radical as hereinbefore defined.

According to a further feature of the present invention there is provided a process for the generation of singlet oxygen by irradiation in the presence of oxygen of a substituted phthalocyanine, in which at least one of the peripheral carbon atoms in the 1–16 positions of the phthalocyanine nucleus ($M_RPc$), as shown in Formula (1), wherein M and k are as hereinbefore defined, is linked via an oxygen atom to an organic radical, the remaining peripheral carbon atoms being unsubstituted or substituted by any combination of atoms or groups and sulphonated derivatives thereof with electromagnetic radiation of wavelength from 650 to 800 nm. Suitable sources of electromagnetic radiation includes sunlight and lasers with emissions in the 650–800 nm region.

According to a further feature of the present invention there are provided phthalocyanine compounds of the Formula (2):

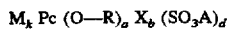  Formula (2)

wherein:

$M_kPc$ is a phthalocyanine nucleus as defined in Formula (1);

each R independently is an organic radical;

each X independently is halogen or hydrogen; the O—R and X groups being attached to one or more of the 16 peripheral carbon atoms of the phthalocyanine nucleus;

A is selected from H, a metal, ammonium or substituted ammonium as described above;

a is from 1 to 16;

b is from 0 to 15;

d is an average value from 0.1 to 50;

a+b is from 1 to 16;

except for $CuPc(O—Ph)_4Cl_{12}$ sulphonic acid containing 9.3% S and the sodium salt thereof.

In phthalocyanines of Formula (2) M is any of the metals, halometal groups, hydroxymetal groups or oxymetal groups described above for M. It is preferred that when M is Cu, R is phenyl, a is 4, and b is 12, that d is an average of from 0.1 to 5.2 or from 5.6 to 50.

In phthalocyanines of Formula (2) it is preferred that M is Ba, Li, Na, K, Mg, ClAl, OHAl, Ca, Zn, ClGa, H, Pt, Pd, OHRh and it is especially preferred that M is Zn, H, ClAl, OHAl, Pt, Pd, ClGa, OHRh and BrIn.

In a phthalocyanine of Formula (2) each of the radicals denoted by R may be selected from any of the pendant organic radicals hereinbefore defined in relation to Formula (1) above.

In a phthalocyanine of Formula (2) it is preferred that a is from 4 to 16 and more preferably from 5 to 16. It is especially preferred that a is 16.

In a phthalocyanine of Formula (2) each halogen denoted by X is preferably independently selected from —F, —Cl, —Br and —I and it is especially preferred that each halogen denoted by X is independently —Cl or —Br.

In a phthalocyanine of Formula (2) it is preferred that b is from 0 to 12, and more preferably from 0 to 11.

When a+b is <16 the remainder of the 16 peripheral carbon atoms, not carrying a group O—R or X, may carry a sulphonate group, —$SO_3A$ or a group represented by R. It is however preferred that the sum of a+b is 16. It is also preferred that a is 4, 8, 12 or 16 and especially 8, 12 or 16.

In phthalocyanines of Formula (2) the metal ion denoted by A is preferably an alkali or alkaline earth metal ion and more preferably is selected from lithium, sodium and potassium ion. It is especially preferred that A is a sodium, an ammonium ion or hydrogen.

In phthalocyanines of Formula (2) it is preferred that d is an average value from 2 to 40. It is more preferred that d is an average value from 2 to 30, especially preferred that d is an average value from 16 to 30.

A preferred sub-group of compounds of Formula (2) are those in which M is Zn, ClAl, OHAl, R is phenyl, 2-, 3- or 4-methylphenyl or naphth-2-yl, a is from 1 to 16, X is halogen, b is from 0 to 15, a+b is equal to 16, A is as hereinbefore defined and d is an average value from 10 to 30. An especially preferred sub-group of compounds of Formula (2) are those in which M is Zn, R is phenyl, 2-, 3- or 4-methylphenyl or naphth-2-yl, a is 4, 12 or 16, b is 12, 4 or 0, a+b is equal to 16, A is as hereinbefore defined and d is an average value from 12 to 30.

According to a further feature of the present invention there are provided phthalocyanine compounds of the Formula (3) free from sulphonic acid groups:

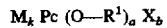  Formula (3)

wherein:

$M_kPc$ is as defined in Formula (1);

$R^1$ is selected from optionally substituted aryl and optionally substituted heteroaryl;

X is halogen or H;
a is an integer from 1 to 16;
b is an integer from 0 to 15; and
a+b is equal to 16;
except for the compounds:
VOPc(4-CH$_3$Ph—O)H$_{15}$
H$_2$Pc(4-(CH$_3$)$_2$PhC—Ph—O)H$_{15}$
CuPc(4-BuPh—O)$_4$H$_{12}$
H$_2$Pc(4-BuPh—O)$_4$H$_{12}$
CuPc(4-(CH$_3$)$_2$PhC—Ph—O)$_4$H$_{12}$
NiPc(4-(CH$_3$)$_2$PhC—Ph—O)$_4$H$_{12}$
PdPc(4-(CH$_3$)$_2$PhC—Ph—O)$_4$H$_{12}$
PtPc(4-(CH$_3$)$_2$PhC—Ph—O)$_4$H$_{12}$
ZnPc(4-(CH$_3$)$_2$PhC—Ph—O)$_4$H$_{12}$
CoPc(4-(CH$_3$)$_2$PhC—Ph—O)$_4$H$_{12}$
FePc(4-(CH$_3$)$_2$PhC—Ph—O)$_4$H$_{12}$
MnPc(4-(CH$_3$)$_2$PhC—Ph—O)$_4$H$_{12}$
H$_2$Pc(4-(CH$_3$)$_2$PhC—Ph—O)$_4$H$_{12}$
MgPc(4-(CH$_3$)$_2$PhC—Ph—O)$_4$H$_{12}$
PbPc(4-(CH$_3$)$_2$PhC—Ph—O)$_4$H$_{12}$
CuPc(Ph—O)$_4$H$_{12}$
ZnPc(Ph—O)$_4$H$_{12}$
H$_2$Pc(Ph—O)$_4$H$_{12}$
VOPc(Ph—O)$_4$H$_{12}$
SnCl$_2$Pc(Ph—O)$_4$H$_{12}$
ZnPc(4-NO$_2$Ph—O)$_4$H$_{12}$
ZnPc(4-NH$_2$Ph—O)$_4$H$_{12}$
H$_2$Pc(4-NH$_2$Ph—O)$_4$H$_{12}$
ZnPc(4-OHPh—O)$_4$H$_{12}$
H$_2$Pc(4-OHPh—O)$_4$H$_{12}$
NiPc(2,3,5-(Me)$_3$Ph—O)$_4$H$_{12}$
PbPc(2-Br-4-EtPh—O)$_4$H$_{12}$
VOPc(2-Br-4-EtPh—O)$_4$H$_{12}$
PbPc(2-Br-4-Me(CH$_2$)$_4$Ph—O)$_4$H$_{12}$
MgPc(2-Br-4-Me(CH$_2$)$_4$Ph—O)$_4$H$_{12}$
ZnPc(4-Me(CH$_2$)$_6$Ph—O)$_4$H$_{12}$
ClAlPc(2-Br-4-Me(CH$_2$)$_3$Ph—O)$_4$H$_{12}$
PbPc(2-Br-4-Me(CH$_2$)$_3$Ph—O)$_4$H$_{12}$
CuPc(2-naphthyl-O)$_8$H$_8$
CoPc(2-naphthyl-O)$_8$H$_8$
ClAlPc(2-naphthyl-O)$_8$H$_8$
Li$_2$Pc(2-naphthyl-O)$_8$H$_8$
TiOPc(2-naphthyl-O)$_8$H$_8$
CuPc(Ph—O)$_8$H$_8$
ClGaPc(Ph—O)$_8$H$_8$
CuPc(4-EtPh-O)$_8$H$_8$
H$_2$Pc(4-MeOPh—O)$_8$H$_8$
CuPc(Ph—O)$_4$Cl$_{12}$
CuPc(4-ClPh—O)$_4$Cl$_{12}$
CuPc(4-CH$_3$Ph—O)$_4$Cl$_{12}$
CuPc(4-Ph—Ph—O)$_4$Cl$_{12}$
CuPc(4-BuPh—O)$_4$Cl$_{12}$
CuPc(Ph—O)$_8$Cl$_8$
ClGaPc(Ph—O)$_8$Cl$_8$
ClAlPc(2-naphthyl-O)$_8$Cl$_8$
CuPc(Ph—O)$_{16}$
H$_2$Pc(Ph—O)$_{16}$
BrAlPc(Ph—O)$_{16}$
ClGaPc(Ph—O)$_{16}$
VOPc(Ph—O)$_{16}$
BrAlPc(4-ClPh—O)$_{16}$
H$_2$Pc(4-CH$_3$Ph—O)$_{16}$
CuPc(2-naphthyl-O)$_{16}$
VOPc(2-naphthyl-O)$_{16}$
SnOPc(2-naphthyl-O)$_{16}$
ClInPc(2-naphthyl-O)$_{16}$ According to a further feature of the present invention there are provided phthalocyanine compounds of the Formula (3):

(1) wherein
M is selected from Na, Ca, ClSc, OHSc, Cr, ClCr, OHCr, Rh, ClRh, OHRh, Sn, Ba, Ir, Sm, ClSm, OHSm, OHAl, SiCl$_2$, SiO and Si(OH)$_2$.
(2) wherein:
M is selected from Li, Na, Mg, Al, OHAl, Ca, Mn, Fe, Co, Zn, Ga, SiCl$_2$, SiO, Si(OH)$_2$;
X is halogen;
a is 4, 8, 12 or 16; and b is 12, 8, 4 or 2.
(3) wherein:
M is selected from H, BrAl, ClGa, ClIn, VO, SnO, Li, Na, Mg, Al, OHAl, Ca, Mn, Fe, Co, Zn, Ga, SiCl$_2$, SiO, Si(OH)$_2$;
X is halogen;
a is 4, 8 or 12; and b is 12, 8 or 4.
(4) wherein:
M is selected from BrAl, ClIn, SnO, Na, Al, OHAl, Ca, SiCl$_2$, SiO and Si(OH)$_2$;
X is hydrogen;
a is 4, 8 or 12; and b is 12, 8 or 4.
(5) wherein:
M is selected from Na, Mg, Al, OHAl, Ca, Mn, Ni, Fe, Zn, SiCl$_2$, SiO and Si(OH)$_2$;
X is hydrogen;
a is 8 or 12; and b is 8 or 4.
(6) wherein:
M is selected from Zn, Mg, Fe, Mn, Pd, Pt, TiO, Ni, Pb, and SnCl$_2$;
a is from 5 to 16; and b is from 11 to 0.
(7) wherein:
M is selected from Zn, Mg, Fe, Fin, Pd, Pt, TiO, Ni, and SnCl$_2$;
a is from 1 to 3, and b is from 15 to 3.
(8) wherein:
M is selected from Zn, Li, Mg, Na, OHAl, Ca, Fe, Mn, Co, Ni, Pb, SnCl$_2$ and VO;
X is halogen;
a is from 1 to 16; and b is from 15 to 0.
(9) wherein:
a is from 1 to 14; and b is from 15 to 2, provided that at least one X is H and one X is halogen.
(10) wherein:
M is H;
X is halogen;
a is from 1 to 15 and b is from 15 to 1.
(11) wherein:
M is H; and
a is 16 provided that R$^1$ is not Ph or 4-MePh.

(12) wherein

M is BrAl; and a is 16 provided that $R^1$ is not Ph or 4Cl—Ph.

(13) wherein:

M is ClAl;

X is halogen;

a is from 1 to 7 or from 9 to 16; and b is from 15 to 9 or from 9 to 0.

(14) wherein:

M is ClAl;

a is 8; b is 8; provided that $R^1$ is not 2-naphthyl.

(15) wherein:

M is Li;

a is from 0 to 16; b is 15 to 0; provided that $R^1$ is not 2-naphthyl.

In a phthalocyanine of Formula (3) it is preferred that each of the radicals denoted by $R^1$ is independently selected from mono- or bi-cyclic aromatic or heteroaromatic radicals. Examples of suitable aromatic and heteroaromatic radicals are those described above for R. The radicals denoted by $R^1$ are more preferably phenyl or naphthyl, especially 2-naphthyl. Preferred substituents for the $R^1$ group are as described for R.

In a phthalocyanine of Formula (3) it is preferred that a is an integer from 4 to 16 and that b is an integer from 12 to 0. It is also preferred that a is 4, 8, 12 or 16, more especially 8, 12 or 16, and that b is 12, 8, 4 or 0.

In a phthalocyanine of Formula (3) it is preferred that the metal denoted by M is Zn, ClAl, OHAl, ClRh, OHRh, ClIn, BrIn, OHIn, ClGa, OHGa, Pt, Pd, Li, Na, K, Ca, Ba, Mg, ClSc or OHSc.

It is especially preferred in phthalocyanines of Formula (3) that M is Zn, ClAl, OHAl, $R^1$ is phenyl or 2-naphthyl, a is 16, ClRh, OHRh, BrIn, OHIn, ClGa, OHGa, Pt or Pd.

A preferred sub-group of compounds of Formula (3) are those in which M is Zn or Mg, $R^1$ is phenyl, 2-, 3- or 4-methylphenyl or naphth-2-yl and a is 16. A further preferred sub-group of compounds of Formula (3) are those in which M is Zn, Mg, ClAl or OHAl, $R^1$ is phenyl, 2-, 3- or 4-methylphenyl or naphth-2-yl, a is 4, X is halogen and b is 12. A further preferred sub-group of compounds of Formula (3) are those in which M is Zn or Mg, $R^1$ is phenyl, 2-, 3- or 4-methylphenyl or naphth-2-yl, a is 8, X is H or halogen and b is 8. A further preferred sub-group of compounds are Formula (3) are those in which M is Zn, Mg, OHAl, ClAl, $R^1$ is phenyl, 2-, 3- or 4-methylphenyl or naphth-2-yl, a is 12, X is H or halogen and b is 8.

The phthalocyanines of Formula (1), Formula (2) and Formula (3) can be prepared by the following methods:

(a) by reaction of a 1,2-dicyanobenzene of Formula (4):

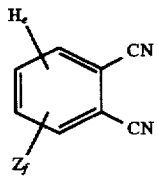

Formula (4)

wherein:

Z is selected from chloro, bromo and iodo;

e is an integer from 0 to 3;

f is an integer from 1 to 4; and e+f is equal to 4 with a compound R—OH whereby up to 4 of the groups, Z, are replaced by R—O groups to form a compound of Formula (5):

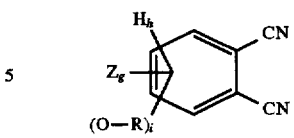

Formula (5)

wherein:

Z is as described above;

R is as described above for compounds of Formula (2);

g is an integer from 0 to 3;

h is an integer from 0 to 3;

i is an integer from 1 to 4; and g+h+i is equal to 4.

followed by reaction of one or more 1,2-dicyanobenzene compounds of Formula (5), or a combination of one or more compounds of Formula (5) and 1,2-dicyanobenzene, with an appropriate metal or metal salt optionally in an inert liquid at an elevated temperature to form a phthalocyanine of Formulae (1), (2) or (3). The presence of at least one equivalent of 1,2-dicyanobenzene is required for the preparation of Formulae (2) and (3) where X is H and b is 13, 14 or 15.

(b) by reaction at elevated temperatures of a compound of Formula (6):

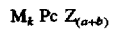  Formula (6)

$M_k$, Pc, Z, a and b are as described above with a compound, R—OH, in a polar organic medium preferably in the presence of an acid binder.

The reactions in (a) above are more fully described in UK patent numbers 1489394 and 2200650 and German patent number 2455675, reaction (b) is more fully described in our co-pending UK patent application number 9023893.2 (incorporated by reference herein).

In reactions of type (b) the polar organic medium which may or may not be a liquid at ambient temperature and which may only partially dissolve the reactants, preferably has a boiling point from 80° C. to 300° C., more preferably from 150° C. to 200° C. The polar organic medium is preferably inert or may act to catalyse the reaction. It is preferred that the polar organic medium is selected from N-methyl-2-pyrrolidone, dimethylformamide, methylcyclohexanol, octanol, benzyl alcohol, nitrobenzene and quinoline. It is especially prefrred that in reactions of type (b) that the polar organic medium is dimethylformamide or N-methyl-2-pyrrolidone.

In reactions of type (b) the acid binder is preferably selected from alkali metal hydroxides and carbonates. It is preferred that the acid binder is lithium, sodium or potassium hydroxide, it is especially preferred that the acid binder is potassium hydroxide.

The sulphonated phthalocyanines of Formula (2) can be prepared by sulphonating a precursor of a phthalocyanine of Formula (2) in which d is 0, using sulphuric acid which may contain excess $SO_3$ (oleum). The strength of acid may vary within wide limits from 1% sulphuric acid up to 30% oleum. It is preferred that the strength of acid is from 50% sulphuric acid up to 30% oleum, it is especially preferred that the strength of acid is from 98% sulphuric to 30% oleum. The reaction temperature may vary from −10° C. to 60° C. depending on the extent of sulphonation required. Sulphonation may be performed in an inert liquid.

As the concentration of the sulphuric acid or the oleum is increased at a fixed reaction temperature, more sulphonic acid groups are introduced into the phthalocyanine. Similarly as the reaction temperature is increased at a particular acid strength, more sulphonic acid groups are introduced into the phthalocyanine.

In the sulphonation reaction a preferred acid is 10% oleum and a preferred reaction temperature is from −10° C. to 40° C., especially from 10° C. to 25° C.

The phthalocyanines can be sulphonated directly on the Pc nucleus, particularly when any of the 1–16 positions is unsubstituted (i.e. the 1–16 peripheral carbon atoms carry a hydrogen atom) or on any of the pendant organic groups R or $R^1$, or on both the Pc nucleus and the pendant organic groups.

The phthalocyanines of particular interest are those which promote the generation of singlet oxygen when exposed to radiation from the 650 nm to 800 nm region, especially the 680 to 770 nm region of the electromagnetic spectrum.

Singlet oxygen has a greater energy than ground-state, triplet oxygen. The singlet and triplet states of oxygen are distinguished by the singlet state having two electrons of anti-parallel spins and the triplet state having an uncoupled pair of electrons with parallel spins. The singlet oxygen is also distinguished from triplet oxygen because it is a highly reactive species with a lifetime from a few microseconds to several hundred microseconds. During its lifetime singlet oxygen has the potential to react before being deactivated. The reactivity of the singlet oxygen may be utilised in a wide range of applications which include photobleaching, photodeodorising, photodynamic therapy (PDT), treatment of visible stains on a range of material surfaces, surfaces include fabric, cement, stone, brick, glass, etc., biocidal, degradation of plastics, paper and pulp bleaching, environmental clean-up, anti-microbial action on fibres, incorporation into various products for example in fabrics as deodorisers, into paints or film treatments to destroy micro-organisms or contaminants, into cement products, glass products and paints to confer self-cleaning properties, sterilising swimming pools and as a surface treatment to prevent yellowing/discoloration of paper. For photobleaching and photodeodorising application the present phthalocyanine can be incorporated into detergent formulations which are used in a wide range of cleaning applications.

According to a further feature of the present invention there is provided a process for removing stains from fabrics which comprises treating the stained fabrics with an aqueous composition comprising at least one compound of Formula (1), Formula (2) or Formula (3) the fabrics being exposed to daylight during or following the treatment.

The aqueous composition may also comprise detergents such as soap or synthetic detergents, other detergent additives such as soil suspending agents, optical brightening agents, sud or foam control agents, perfume, surfactants such as alkyl sulphonates, paraffin sulphonates and alkylbenzene sulphonates, ethoxylated alcohols or betaines, and alkaline detergency builders such as sodium carbonate, silicate, orthophosphates and polyphosphates.

The process for removing stains is preferably carried out at temperatures from 10° C. to 80° C., more preferably from 20° C. to 60° C. and especially from 35° C. to 45° C. Suitable process times for stain removal are typically from 5 minutes to 5 hours, preferably from 10 minutes to 1 hour.

The aqueous composition preferably contains from 0.0005 g to 0.1 g per liter of compounds of Formula (1), Formula (2) and/or Formula (3), more preferably from 0.001 g/l to 0.01 g/l.

The efficacy of the stain removal process generally depends on the concentration of compounds of Formula (1), Formula (2) and/or Formula (3) in the wash solution, the intensity of daylight, the process temperature and the process time. The process is generally more effective with higher concentrations of compounds of Formula (1), Formula (2) and/or Formula (3), at higher intensities of daylight at higher process temperatures and with longer process times.

The preferred compounds of Formula (2) and Formula (3) are those where $M_k$ is Zn, Co, Fe, Ca, ClAl, OHAl, and $H_2$; R or $R^1$ is phenyl and 2-naphthyl; a is 16; and d is from 16 to 30.

According to a further feature of the present invention there are provided compounds of the Formulae (1), (2) and (3) for use in therapeutic treatment of a human or an animal body.

According to a further feature of the present invention, compounds of Formula (1), Formula (2) or Formula (3) are used for the manufacture of a medicament for use in the treatment of skin and subcutaneous cancers by photodynamic therapy.

In this treatment the compound of Formula (1), Formula (2) or Formula (3) is introduced into the affected tissue and then irradiated with electromagnetic radiation in the region from 650–800 nm, preferably 680–770 nm in order to generate singlet oxygen which destroys the affected cells.

The phthalocyanine compounds of the present invention promote the formation of singlet oxygen under the influence of electromagnetic radiation, particularly in the 680–770 nm region and are capable of promoting singlet oxygen formation in localised areas.

Measurement of triplet oxygen yields after laser excitation and singlet oxygen emission yields allows calculation of singlet oxygen generating efficiency (SΔ). The experimental details for these measurements are more fully described in Gorman et al. Journal of the American Chemical Society [1987], 109, 3091; Gorman et al. Journal of the American Chemical Society [1989], 111, 1876 and Gorman et al. Photochemistry and Photobiology [1987] 45(2), 215.

The invention is further illustrated by the following examples in which all parts and percentages are by weight unless otherwise indicated.

EXAMPLE 1

Preparation of hexadeca(phenoxy) dihydrophthalocyanine (i) Preparation of 1,2-dicyano-3,4,5,6-tetraphenoxybenzene A mixture of 1,2-dicyano-3,4,5,6-tetrachlorobenzene (50 parts), phenol (106 parts), potassium carbonate (104 parts) and dimethylformamide (200 parts) was stirred and heated at 70° C. for 2 hours before pouring into water (500 parts). The aqueous mixture was extracted with chloroform (2×300 parts). The chloroform extract was washed with a 5% aqueous solution of sodium hydroxide (2×250 parts) and then with water (2×250 parts). The chloroform extract was dried over anhydrous magnesium sulphate, filtered and the chloroform was removed by distillation under reduced pressure to leave a brown oil. The brown oil was dissolved in hot butan-1-ol and allowed to cool slowly. 1,2-Dicyano-3,4,5,6-tetraphenoxybenzene (62.2 parts, 67%) was obtained as a pale yellow solid m.p. 149°–151° C.

(ii) Preparation of hexadeca(phenoxy) dilithium phthalocyanine

Lithium (0.42 parts) was dissolved in butan-1-ol (50 parts) with stirring at 100° C. over 4 hours before adding 1,2-dicyano-3,4,5,6-tetra(phenoxy)benzene (10 parts). The reaction mixture was stirred at 120° C. for 30 minutes. The solution was cooled and a green solid was collected by filtration. The solid was washed with methanol (3×50 parts) and dried to give hexadeca(phenoxy)dilithium phthalocyanine (5.5 parts) m.p.>250° C.

(iii) Preparation of hexadeca(phenoxy) dihydrophthalocyanine

A mixture of hexadeca(phenoxy) dilithium phthalocyanine (3.0 parts) and toluene (100 parts) was stirred at 20° C. and p-toluene sulphonic acid (1.14 parts) was added slowly. The reaction mixture was stirred at 20° C. for 30 minutes before adding activated carbon and filtering through Clarcel flo filter aid. After filtering the solution was passed through a silica gel column washing with toluene. The solvent was removed by distillation under reduced pressure to leave a green solid. The solid was stirred in methanol (50 parts), filtered off and washed with water and dried to give hexadeca(phenoxy) dihydrophthalocyanine (2.68 parts) m.p.>250° C.

EXAMPLE 2

Preparation of hexadeca(phenoxy) zinc phthalocyanine

A mixture of 1,2-dicyano-3,4,5,6-tetra(phenoxy)benzene (20 parts), zinc chloride (1.81 parts), urea (0.8 parts) and nitrobenzene (40 parts) was stirred at 180° C. for 2 hours before pouring into ethanol (74 OP, 200 parts), aqueous hydrochloric acid (2 mol.dm$^{-3}$, 600 parts), aqueous ammonia (2 mol.dm$^{-3}$, 300 parts), water (2×200 parts) and ethanol (74 OP, 500 parts). The solid was dried to give hexadeca (phenoxy) zinc phthalocyanine (4.4 parts) m.p.>250° C.

EXAMPLE 3

Preparation of hexadeca(phenoxy) chloroaluminium phthalocyanine

A mixture of 1,2-dicyano-3,4,5,6-tetra(phenoxy)benzene (4.13 parts), urea (0.17 parts), anhydrous aluminium chloride (0.37 parts) and ammonium molybdate (0.004 parts) was stirred at 200° C. for 30 minutes and cooled to give a brown solid. The solid was broken up and slurried in ethanol (74 OP, 200 parts). A green solid was collected by filtration and washed with ethanol (100 parts) before slurrying it with aqueous hydrochloric acid (2 mol.dm$^{-3}$ 200 parts) and filtering. The solid was washed with aqueous ammonia (2 mol.dm$^{-3}$, 100 parts), water (200 parts) and ethanol (74 OP, 300 parts). The solid was slurried in hot ethanol (74 OP, 2×200 parts), collected and dried to give hexadeca(phenoxy) chloroaluminium phthalocyanine (1.17 parts) m.p. 152°–154° C.

EXAMPLE 4

Preparation of hexadeca(phenoxy) magnesium phthalocyanine

The procedure of Example 3 was used except that magnesium chloride hexahydrate (0.56 parts) was used in place of the anhydrous aluminium chloride. Hexadeca(phenoxy) magnesium phthalocyanine (1.57 parts) was obtained as a green solid, m.p.>250° C.

EXAMPLE 5

Preparation of hexadeca(phenoxy) copper (II) phthalocyanine

The procedure of Example 3 was used except that copper (II) chloride (0.34 parts) was used in place of the anhydrous aluminium chloride. Hexadeca(phenoxy) copper (II) phthalocyanine (3.6 parts) was obtained as a green solid, m.p.>250° C.

EXAMPLE 6

Preparation of hexadeca(phenoxy) nickel (II) phthalocyanine

The procedure of Example 3 was used except that nickel (II) chloride (0.36 parts) was used in place of the anhydrous aluminium chloride. Hexadeca(phenoxy) nickel (II) phthalocyanine (1.1 parts) was obtained as a green solid, m.p.>250° C.

EXAMPLE 7

Preparation of hexadeca(2-naphthoxy)dilithium phthalocyanine (i) Preparation of 1,2-dicyano-3,4,5,6-tetra(2-naphthoxy) benzene 1,2-Dicyano-3,4,5,6-tetrachlorobenzene (30.5 parts), potassium carbonate (62.8 parts) and 2-naphthol (98.1 parts) were stirred in dimethylformamide (140 parts) at 70° C. for 3 hours. The mixture was poured into water (300 parts) and extracted with chloroform (3×300 parts). The combined chloroform extracts were washed with dilute aqueous sodium hydroxide solution (500 parts) and then with water (500 parts). The chloroform was dried over anhydrous magnesium sulphate before evaporating under reduced pressure to leave a brown liquid which crystallised on adding butan-1-ol, cooling and standing for 2 hours. The crystallised solid was filtered, washed with butan-1-ol until the filtrates were colourless. The solid was dried to give 1,2-dicyano-3,4,5,6-tetra(2-naphthoxy)benzene (40.6 parts), m.p. 188°–190° C.

(ii) Preparation of hexadeca(2-naphthoxy) dilithium phthalocyanine

The procedure of Example 1(ii) was used except that 1,2-dicyano-3,4,5,6-tetra(2-naphthoxy)benzene (10 parts) was used in place of the 1,2-dicyano-3,4,5,6-tetra(phenoxy) benzene and 0.3 parts instead of 0.42 parts of lithium were used. Hexadeca(2-naphthoxy) dilithium phthalocyanine (5.71 parts) was obtained as a green solid, m.p. 185°–190° C.

EXAMPLE 8

Preparation of hexadeca(2-naphthoxy) zinc phthalocyanine

The procedure of Example 2 was used except that 1,2-dicyano-3,4,5,6-tetra(2-naphthoxy)benzene (20 parts) was used in place of the 1,2-dicyano-3,4,5,6-tetra(phenoxy) benzene and 1.29 parts instead of 1.81 parts of zinc chloride and 0.57 parts instead of 0.8 parts of urea were used. Hexadeca(2-naphthoxy) zinc phthalocyanine (15.4 parts) was obtained as a green solid, m.p. 230°–235° C.

EXAMPLE 9

Preparation of hexadeca(phenoxy)dihydrophthalocyanine eicosa (sulphonic acid) sodium salt Hexadeca(phenoxy)dihydrophthalocyanine (1.0 parts) was added to 10% oleum (2.3 parts) at 0° C. over 15 minutes, the mixture was allowed to warm to 20° C. and was stirred for 3 hours before pouring into a mixture of ice and water (100 parts). The resultant solution was neutralised to pH 7 using 48% aqueous sodium hydroxide. The product was purified by dialysing the neutralised solution in Visking tubing (obtainable from The Scientific Instrument Centre, Eastleigh, Hampshire) over 24 hours. The dialysed solution was evaporated to leave hexadeca (phenoxy) dihydrophthalocyanine eicosa (sulphonic acid) sodium salt (2.0 parts) as a black solid, m.p.230°–235° C.

EXAMPLE 10

Preparation of hexadeca(2-naphthoxy) dihydro phthalocyanine triaconta (sulphonic acid) sodium salt The procedure of Example 9 was used except that 2.6 parts instead of 2.3 parts of 10% oleum was used. Hexadeca (phenoxy)dihydro phthalocyanine eicosa(sulphonic acid) sodium salt was obtained as a black solid, m.p.>250° C.

EXAMPLE 11

Preparation of hexadeca(phenoxy) zinc phthalocyanine hexadeca(sulphonic acid) sodium salt The procedure of Example 9 was used except that hexadeca(phenoxy) zinc phthalocyanine (1.4 parts) was used in place of the hexadeca(phenoxy) dihydro phthalocyanine and 3.5 parts of 10% oleum was used instead of 2.3 parts. Hexadeca(phenoxy) zinc phthalocyanine hexadeca (sulphonic acid) sodium salt (1.32 parts) was obtained as a green solid, was obtained as a green solid, m.p.>250° C.

EXAMPLE 12

Preparation of hexadeca(2-naphthoxy) zinc phthalocyanine triaconta(sulphonic acid) sodium salt The procedure of Example 9 was used except that hexadeca(2-naphthoxy) zinc phthalocyanine (1.0 parts) was used in place of the hexadeca(phenoxy) dihydro phthalocyanine and 3.0 parts of 10% oleum was used instead of 2.3 parts. Hexadeca(2-naphthoxy) zinc phthalocyanine triaconta (sulphonic acid) sodium salt (1.7 parts) was obtained as a green solid, m.p.>250° C.

EXAMPLE 13

Preparation of hexadeca(2-naphthoxy)hydroxyaluminium phthalocyanine triaconta(sulphonic acid) sodium salt (i) Preparation of hexadeca(2-naphthoxy) chloroaluminium phthalocyanine The procedure of Example 3 was used except that 1,2-dicyano-3,4,5,6-tetra(2-naphthoxy)benzene (3.0 parts) was used in place of the 1,2-dicyano-3,4,5,6-tetra(phenoxy) benzene, 0.20 parts instead of 0.37 parts of anhydrous aluminium chloride and 0.09 parts instead of 0.17 parts of urea were used. Hexadeca(2-naphthoxy) chloroaluminium phthalocyanine (2.43 parts) was obtained as a brown-green solid, m.p.208°–210° C.

(ii) Preparation of hexadeca(2-naphthoxy) hydroxyaluminium phthalocyanine triaconta(sulphonic acid) sodium salt The procedure of Example 9 was used except that hexadeca(2-naphthoxy) chloroaluminium phthalocyanine (1.0 parts) was used in place of the hexadeca(phenoxy) dihydro phthalocyanine. Hexadeca(2-naphthoxy) zinc phthalocyanine triaconta(sulphonic acid) sodium salt (1.7 parts) was obtained as a green solid,m.p.>250° C.

EXAMPLE 14

Preparation of hexadeca(phenoxy) hydroxyaluminium phthalocyanine hexadeca(sulphonic acid) sodium The procedure of Example 9 was used except that hexadeca(phenoxy) chloroaluminium phthalocyanine (0.4 parts) was used in place of the hexadeca(phenoxy) dihydro phthalocyanine, 3.0 parts instead of 2.3 parts of 10% oleum was used. Hexadeca(phenoxy) hydroxyaluminium phthalocyanine hexadeca(sulphonic acid) sodium salt (0.63 parts) was obtained as a green solid, m.p.>250° C.

EXAMPLE 15

Preparation of hexadeca(2-naphthoxy) dihydro phthalocyanine triaconta(sulphonic acid) sodium salt (i) Preparation of hexadeca(2-naphthoxy) dihydro phthalocyanine The procedure of Example 1(iii) was used except that hexadeca(2-naphthoxy) dilithium phthalocyanine (3.0 parts) was used in place of the hexadeca(phenoxy) dilithium phthalocyanine and 0.82 parts instead of 1.14 parts of p-toluene sulphonic acid were used. Hexadeca(2-naphthoxy) dihydro phthalocyanine (0.75 parts) was obtained as a black solid, m.p. 220°–225° C.

(ii) Preparation of hexadeca(2-naphthoxy) dihydro phthalocyanine triaconta(sulphonic acid) sodium salt The procedure of Example 9 was used except that hexadeca(2-naphthoxy) dihydro phthalocyanine (1.0 parts) was used in place of the hexadeca(phenoxy) dihydro phthalocyanine, 3.0 parts instead of 2.3 parts of 10% oleum was used. Hexadeca(2-naphthoxy) dihydro phthalocyanine triconta(sulphonic acid) sodium salt (1.5 parts) was obtained as a green solid, m.p.>250° C.

EXAMPLE 16

Preparation of hexadeca(phenoxy) palladium phthalocyanine

The procedure of Example 2 was used except that palladium (II) chloride (2.4 parts) was used in place of the zinc chloride. Hexadeca (phenoxy) palladium phthalocyanine was obtained as a green solid, m.p.>250° C.

EXAMPLE 17

Preparation of hexadeca(phenoxy) palladium phthalocyanine hexadeca (sulphonic acid) sodium salt The procedure of Example 9 was used except that hexadeca(phenoxy) palladium phthalocyanine was used in place of the hexadeca(phenoxy) dihydro phthalocyanine. Hexadeca(phenoxy) palladium phthalocyanine hexadeca (sulphonic acid) sodium salt was obtained as a green solid, m.p.>250° C.

EXAMPLE 18

Preparation of hexadeca(phenoxy) platinum phthalocyanine

The procedure of Example 2 was used except that platinum (II) bromide (4.7 parts) was used in place of the zinc chloride. Hexadeca (phenoxy) platinum phthalocyanine was obtained as a green solid, m.p.>250° C.

EXAMPLE 19

Preparation of hexadeca(phenoxy) platinum phthalocyanine hexadeca (sulphonic acid) sodium salt The procedure of Example 9 was used except that hexadeca(phenoxy) platinum phthalocyanine was used in place of the hexadeca(phenoxy) dihydro phthalocyanine. Hexadeca(phenoxy) platinum phthalocyanine hexadeca (sulphonic acid) sodium salt was obtained as a green solid, m.p.>250° C.

EXAMPLE 20

Preparation of hexadeca(phenoxy) chlororuthenium phthalocyanine

The procedure of Example 2 was used except that ruthenium (III) chloride (2.8 parts) was used in place of the zinc chloride. Hexadeca (phenoxy) chlororuthenium phthalocyanine was obtained as a green solid, m.p.>250° C.

The 1,2-dicyanobenzenes of Examples 24–36 are not a feature of the present invention but are used as intermediates in the preparation of phthalocyanines described below.

EXAMPLES 24 TO 30

Further 1,2-dicyanobenzenes compounds of Formula (5) were prepared by the method of Example 1i) using equimolar amounts of the appropriate substituted phenol in place of phenol as described in Example 1i).

| Example | Starting Phenol | Product 1,2-dicyanobenzene |
|---|---|---|
| 24 | 2-methylphenol | 3,4,5,6-tetra(2-methylphenoxy) |
| 25 | 3-methylphenol | 3,4,5,6-tetra(3-methylphenoxy) |
| 26 | 4-methylphenol | 3,4,5,6-tetra(4-methylphenoxy) |
| 27 | 4-methoxyphenol | 3,4,5,6-tetra(4-methoxyphenoxy) |
| 28 | 1-naphthol | 3,4,5,6-tetra(1-naphthoxy) |
| 29 | 2-naphthol | 3,4,5,6-tetra(2-naphthoxy) |
| 30 | 4-chlorophenol | 3,4,5,6-tetra(4-chlorophenoxy) |

EXAMPLE 31

Preparation of 4-chloro-1,2-dicyano-3,5,6-tri(4-methylphenoxy)benzene

The procedure of Example 1i) was followed except that 4-methyl phenol (121.8 parts) was used in place of the phenol. 4-Chloro-1,2-dicyano-3,5,6-tri(4-methylphenoxy) benzene (43.7 parts) was obtained as a pale green solid, m.p. 142°–145° C.

EXAMPLES 32 AND 33

Further 1,2-dicyanobenzenes in accordance with Formula (6) were prepared by the method of Example 21 using equimolar amounts of the appropriate phenol in place of the phenol described in Example 31.

| Example | Starting Phenol | Product 1,2-dicyanobenzene |
|---|---|---|
| 32 | 4-methoxyphenol | 4-chloro-3,5,6-tri(4-methoxyphenoxy) |
| 33 | 4-nitrophenol | 4-chloro-3,5,6-tri(4-nitrophenoxy) |

EXAMPLE 34

Preparation of 3,5,6-trichloro-1,2-dicyano-4-phenoxybenzene

A solution of potassium hydroxide (11.2 parts) in water (22 parts) was added dropwise to a stirred solution of 3,4,5,6-tetra-chloro-1,2-dicyanobenzene (26.6 parts) and phenol (9.4 parts) in acetone (100 arts) at 0° C. The solution was stirred at 60° C. for 2 hours before pouring into water (500 parts). The aqueous mixture was extracted with dichloromethane (3×500 parts). The dichloromethane extracts were washed with water (3×200 parts), dried over anhydrous $Na_2SO_4$, filtered and the dichloromethane was removed under reduced pressure to leave a brown solid. The solid was recrystallised from butan-1-ol. 3,5,6-Trichloro-1,2-dicyano-4-phenoxybenzene (17 parts) was obtained as a brown solid, m.p. 147°–150° C.

EXAMPLE 35

Preparation of 1,2-dicyano-3-phenoxybenzene

A solution of 1,2-dicyano-3-nitrobenzene (2.77 parts) and sodium phenoxide (2.79 parts) in dimethylformamide (50 parts) was stirred at 120° C. for 2 hours. The reaction mixture was poured into water and extracted with diethyl ether (100 parts). The diethyl ether extract was washed with 5% aqueous potassium hydroxide solution (2×200 parts) and water (2×200 parts) and the diethyl ether was removed under reduced pressure to leave a solid. Recrystallisation of the solid from a 1:1 diethyl ether:petroleum spirit (b.pt.60°–80° C.) gave 1,2-dicyano-3-phenoxybenzene (2.1 parts, 60%) as a pale green solid, m.pt.110°–112° C.

EXAMPLE 36

Preparation of 1,2-dicyano-4-phenoxybenzene

The procedure of Example 35 was followed except that 1,2-dicyano-4-nitrobenzene (1.0 part) was used in place of the 1,2-dicyano-3-nitrobenzene, 1.0 parts instead of 2.79 parts of sodium phenoxide and 20 parts instead of 50 parts of dimethylformamide were used. 1,2-Dicyano-4-phenoxybenzene (0.6 parts, 49%) was obtained as a white solid, m.pt.98°–100° C.

EXAMPLES 37–61

Further phthalocyanines of Formula (3) were prepared by the method of Example 3 using equimolar amounts of the appropriate 1,2-dicyanobenzene in place of the 1,2-dicyano-3,4,5,6-tetra(phenoxy)benzene and the appropriate anhydrous metal chloride in place of the anhydrous aluminium chloride:

| | | Metal | Product | | | | Yield | |
|---|---|---|---|---|---|---|---|---|
| Example | 1,2-dicyanobenzene | Chloride | M | $R^1$ | a | x | b | % | m.p./°C. |
| 37 | as Example 1i) | $RhCl_3$ | OHRh | Ph | 16 | — | — | 30 | 135–140 |
| 38 | as Example 1i) | $InBr_3$ | BrIn | Ph | 16 | — | — | 56 | >250 |
| 39 | as Example 1i) | $ScCl_3$ | OHSc | Ph | 16 | — | — | 22 | 190–195 |
| 40 | as Example 1i) | $GaCl_3$ | ClGa | Ph | 16 | — | — | 55 | >250 |
| 41 | as Example 24 | $ZnCl_2$ | Zn | 2-MePh | 16 | — | — | 18 | >250 |
| 42 | as Example 25 | $ZnCl_2$ | Zn | 3-MePh | 16 | — | — | 37 | 139–143 |
| 43 | as Example 26 | $ZnCl_2$ | Zn | 4-MePh | 16 | — | — | 13 | >250 |
| 44 | as Example 24 | $AlCl_3$ | ClAl | 2-MePh | 16 | — | — | 27 | >250 |
| 45 | as Example 25 | $AlCl_3$ | ClAl | 3-MePh | 16 | — | — | 20 | 205–207 |
| 46 | as Example 26 | $AlCl_3$ | OHAl | 4-MePh | 16 | — | — | 26 | >250 |
| 47 | as Example 24 | $MgCl_2$ | Mg | 2-MePh | 16 | — | — | 58 | >250 |
| 48 | as Example 25 | $MgCl_2$ | Mg | 3-MePh | 16 | — | — | 40 | 132–137 |

-continued

| Example | 1,2-dicyanobenzene | Metal Chloride | M | Product R¹ | a | x | b | Yield % | m.p./°C |
|---|---|---|---|---|---|---|---|---|---|
| 49 | as Example 26 | MgCl₂ | Mg | 4-MePh | 16 | — | — | 55 | 223–226 |
| 50 | as Example 30 | ZnCl₂ | Zn | 4-ClPh | 16 | — | — | 21 | 187–190 |
| 51 | as Example 27 | ZnCl₂ | Zn | 4-OMePh | 16 | — | — | 73 | 132–135 |
| 52 | as Example 29 | MgCl₂ | Mg | 2-Np | 16 | — | — | 24 | 175–180 |
| 53 | as Example 29 | AlCl₃ | ClAl | 2-Np | 16 | — | — | 79 | 208–210 |
| 54 | as Example 28 | ZnCl₂ | Zn | 1-Np | 16 | — | — | 18 | 235–240 |
| 55 | as Example 31 | ZnCl₂ | Zn | 4-MePh | 12 | Cl | 4 | 29 | 175–178 |
| 56 | as Example 31 | MgCl₂ | Mg | 4-MePh | 12 | Cl | 4 | 27 | 210–213 |
| 57 | as Example 31 | AlCl₃ | ClAl | 4-MePh | 12 | Cl | 4 | 65 | 175–178 |
| 58 | as Example 32 | ZnCl₂ | Zn | 4-OMePh | 12 | Cl | 4 | 33 | 189–191 |
| 59 | as Example 33 | ZnCl₂ | Zn | 4-NO₂Ph | 12 | Cl | 4 | 15 | 183–185 |
| 60 | as Example 36 | ZnCl₂ | Zn | Ph | 4 | H | 12 | 17 | >250 |
| 61 | as Example 35 | ZnCl₂ | Zn | Ph | 4 | H | 12 | 13 | 178–180 |

EXAMPLE 62

Preparation of hexadeca(1-naphthoxy) zinc phthalocyanine

A mixture of 1,2-dicyano-3,4,5,6-tetra(1-napthoxy)benzene (7.0 parts), zinc chloride (0.45 parts), urea (0.2 parts) and ammonium molybate (0.004 parts) in nitrobenzene (20 parts) was heated at 180° C. for 2 hours before cooling and pouring into ethanol (150 parts, 74 OP). The precipitated green solid was collected by filtration, washed with ethanol (10 parts, 74 OP) and dried to give hexadeca (1-naphthoxy) zinc phthalocyanine (18%), m.p.235°–240° C.

EXAMPLE 63

Preparation of dodecachlorotetra(phenoxy) zinc phthalocyanine

The method of Example 62 was used except that 1,2-dicyano-3,5,6-trichloro-4-phenoxybenzene (3.2 parts) was used in place of the 1,2-dicyano-3,4,5,6-tetra(2-napthoxy)benzene to give dodecachlorotetra(phenoxy) zinc phthalocyanine (20%), m.p.>250° C.

EXAMPLE 64

Preparation of hexadeca(phenoxy) dilithium phthalocyanine

Lithium (0.2 parts) was dissolved in refluxlug propan-2-ol (20 parts) over 3 hours. 1,2-Dicyano-3,4,5,6-tetra(phenoxy)benzene (4.5 parts) was added to the refluxing mixture over 5 minutes and the reaction mixture was refluxed for a further 30 minutes before cooling. Methanol (80 parts) was added to the cooled reaction mixture and the precipitated solid was collected by filtration, washed with methanol (3×20 parts) and dried. Chloroform (50 parts) was added to the dried solid and the mixture was filtered to remove inorganic material. The chloroform was evaporated under reduced pressure to give hexadeca(phenoxy) dilithium phthalocyanine (55%), m.p.>250° C.

EXAMPLES 65–68

Further phthalocyanines of Formula (3) were prepared by the method of Example 64 using equimolar amounts of the appropriate metal in place of the Lithium:

| Example | Metal | M | R¹ | a | x | b | Yield % | m.p./°C |
|---|---|---|---|---|---|---|---|---|
| 65 | K | K₂ | Ph | 16 | — | — | 22 | >250 |
| 66 | Na | Na₂ | Ph | 16 | — | — | 24 | >250 |
| 67 | Ca | Ca | Ph | 16 | — | — | 33 | >250 |
| 68 | Ba | Ba | Ph | 16 | — | — | 24 | >250 |

EXAMPLES 69–75

Further sulphonated phthalocyanines were prepared using the method of Example 11 except that 3.0 parts instead of 10% oleum were used and appropriate molar amounts of the phthalocyanine were used in place of the hexadeca (phenoxy) zinc phthalocyanine:

| | Phthalocyanine of Formula (3) used | | | | | | |
|---|---|---|---|---|---|---|---|
| Example | M | R¹ | a | x | b | Sulphonated Product |
| 69 | Ca | Ph | 16 | — | — | (SO₃Na)₁₆ |
| 70 | Mg | Ph | 16 | — | — | (SO₃Na)₁₆ |
| 71 | Zn | 2-MePh | 16 | — | — | (SO₃Na)₁₆ |
| 72 | Zn | 3-MePh | 16 | — | — | (SO₃Na)₁₆ |
| 73 | Zn | 4-MePh | 16 | — | — | (SO₃Na)₁₆ |
| 74 | OHAl | 4-MePh | 16 | — | — | (SO₃Na)₁₆ |
| 75 | Zn | Ph | 4 | Cl | 12 | (SO₃Na)₄ |

In all the above examples:

Ph=phenyl

2-MePh=2-methylphenyl

3-MePh=3-methylphenyl

4-MePh=4-methylphenyl

4-ClPh=4-chlorophenyl

4-OMePh=4-methoxyphenyl

2-Np=naphth-2-yl

1-Np=naphth-1-yl

4-NO₂Ph=4-nitrophenyl

The ultraviolet, visible and infra red spectra were measured in solvents such as chloroform and dichloromethane and H₂O.

The singlet oxygen generating efficiencies SΔ of non-sulphonated phthalocyanines were measured in benzene, or acetonitrile and of sulphonated phthalocyanines in water.

The max values and S values are shown in Table 1.

TABLE 1

| Example No. | λmax/nm | SΔ % |
| --- | --- | --- |
| 1 | 745 (CHCl₃) | 6 |
| 2 | 726 (CHCl₃) | 43 |
| 3 | 750 (CHCl₃) | 36 |
| 4 | 726 (CHCl₃) | 22 |
| 5 | 726 (CHCl₃) | 4 |
| 6 | 717 (CHCl₃) | 5 |
| 7 | 772 (CHCl₃) | 47 |
| 8 | 730 (CHCl₃) | 111 |
| 9 | 739 (CHCl₃) | 30 |
| 10 | 740 (CHCl₃) | 46 |
| 11 | 720 (CHCl₃) | 110 |
| 12 | 723 (CHCl₃) | 73 |
| 13 | 745 (CHCl₃) | 46 |
| 14 | 738 (H₂O) | 36 |
| 15 | 740 (H₂O) | 46 |
| 16 | 701 (CH₂Cl₂) | 36 |
| 18 | 690 (CH₂Cl₂) | 55 |
| 37 | 694 (CH₂Cl₂) | 32 |
| 38 | 753 (CH₂Cl₂) | 51 |
| 39 | 782 (CH₂Cl₂) | 13 |
| 40 | 750 (CH₂Cl₂) | 52 |
| 41 | 736 (CH₂Cl₂) | 45 |
| 42 | 727 (CH₂Cl₂) | 38 |
| 43 | 725 (CH₂Cl₂) | 45 |
| 44 | 758 (CH₂Cl₂) | 24 |
| 45 | 742 (CH₂Cl₂) | 23 |
| 46 | 753 (CH₂Cl₂) | 34 |
| 47 | 721 (Acetone) | 22 |
| 48 | 723 (CH₂Cl₂) | 24 |
| 49 | 722 (CH₂Cl₂) | 23 |
| 50 | 710 (CH₂Cl₂) | 8 |
| 51 | 751 (CH₂Cl₂) | 15 |
| 52 | 725 (CHCl₃) | 23 |
| 53 | 752 (CHCl₃) | 19 |
| 54 | 736 (CH₂Cl₂) | 34 |
| 55 | 693 (CH₂Cl₂) | 29 |
| 56 | 705 (Acetone) | 21 |
| 57 | 742 (CH₂Cl₂) | 28 |
| 58 | 702 (CH₂Cl₂) | 68 |
| 59 | 690 (CH₂Cl₂) | 46 |
| 60 | 678 (CH₂Cl₂) | 43 |
| 61 | 688 (DMF) | 49 |
| 62 | 736 (CH₂Cl₂) | 34 |
| 63 | 693 (CH₂Cl₂) | 40 |
| 64 | 772 (CHCl₃) | 14 |
| 65 | 742 (CH₂Cl₂) | 13 |
| 66 | 714 (CH₂Cl₂) | 21 |
| 67 | 741 (CH₂Cl₂) | 13 |
| 68 | 717 (H₂O) | 10 |
| 69 | 742 (H₂O) | 8 |
| 70 | 732 (H₂O) | 17 |
| 71 | 726 (H₂O) | 67 |
| 72 | 724 (H₂O) | 52 |
| 73 | 705 (H₂O) | 39 |
| 74 | 736 (H₂O) | 62 |
| 75 | 686 (H₂O) | 6 |

The stain removal aspects of the invention are illustrated by the following examples.

In Examples 76–91 the following procedure was used.

Cotton cloth was cut into 7.5 cm×10 cm pieces and the pieces were stained by allowing them to soak for 2 hours in a tea solution prepared from 2 tea bags and 1 liter of water. The cloth pieces were dried in a tumbler dryer and stored in the dark until needed.

The wash tests were carried out in a stirred metal bath at 40° C. using (i) 9 g of a commercially available biological washing liquid (Ariel) per liter of water or (ii) 3 g. Of a commercially available non-aqueous biological washing liquid (from Marks and Spencer PLC) per liter of water. 0.003 g of a compound of Formula (2) or 0.003 g of a compound of Formula (3) was added per liter of water to provide a wash solution. Three cloth pieces were added to each wash solution and these were stirred at 40° C. for 10 minutes. The cloth pieces were rinsed well with water and dried in direct sunlight. The effect of each compound of Formulae (2) or (3) was assessed by measuring the reflectance of each dried cloth piece and comparing it with an unwashed cloth piece. Reflectance measurements were obtained using a Gardener Colorgard reflectometer. The results were calculated using $$A = \frac{R-U}{U} \times 100$$

where

A=% improvement of washed versus unwashed cloth
R=% reflectance of washed cloth piece
U=% reflectance of unwashed cloth piece.
The results are summarised in Table 2 below.

TABLE 2

| (a) Biological washing liquid | | | |
| --- | --- | --- | --- |
| Example | Compound added to wash solution | | A |
| 76 | None | | 0.8 |
| 77 | ZnPc(2-naphthyl-O)₁₆ | (e.g. 8) | 25.7 |
| 78 | OHAlPc(Ph—O)₁₆(SO₃H)₁₆ | (e.g. 14) | 14.1 |
| 79 | OHAlPc(2-naphthyl-O)₁₆(SO₃H)₃₀ | (e.g. 13) | 16.2 |
| 80 | H₂Pc(2-naphthyl-O)₁₆(SO₃H)₃₀ | (e.g. 15) | 21.9 |
| 81 | ZnPc(Ph—O)₁₆(SO₃H)₁₆ | (e.g. 11) | 31.4 |
| 82 | ZnPc(2-naphthyl-O)₁₆(SO₃H)₃₀ | (e.g. 12) | 31.5 |
| 83 | H₂Pc(Ph—O)₁₆(SO₃H)₂₀ | (e.g. 9 & 10) | 27.5 |

| (b) Non-aqueous biological washing liquid | | | |
| --- | --- | --- | --- |
| Example | Compound added to wash solution | | A |
| 84 | None | | 4.9 |
| 85 | ZnPc(2-naphthyl-O)₁₆ | (e.g. 8) | 29.9 |
| 86 | OHAlPc(Ph-O)₁₆(SO₃H)₁₆ | (e.g. 14) | 17.6 |
| 87 | OHAlPc(2-naphthyl-O)₁₆(SO₃H)₃₀ | (e.g. 13) | 18.1 |
| 88 | H₂Pc(2-naphthyl-O₁₆(SO₃H)₃₀ | (e.g. 15) | 25.8 |
| 89 | ZnPc(Ph-O)₁₆(SO₃H)₁₆ | (e.g. 11) | 25.2 |
| 90 | ZnPc(2-naphthyl-O)₁₆(SO₃H)₃₀ | (e.g. 12) | 26.3 |
| 91 | H₂Pc(Ph-O)₁₆(SO₃H)₂₀ | (e.g. 9 & 10) | 29.6 |

We claim:

1. A process for removing stains from fabrics which comprises treating the stained fabrics with an aqueous composition comprising at least one compound selected from the group consisting of (a) substituted phthalocyanines in which at least one of the peripheral carbon atoms in the 1–16 position of the phthalocyanine nucleus (M$_k$Pc) of Formula (1)

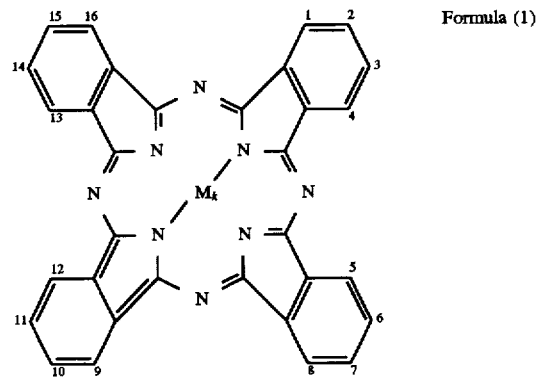

Formula (1)

wherein:

M is selected from H, metal, halometal, oxymetal and hydroxymetal; and k is the inverse of ½ of the valency of M;
is linked via an oxygen atom to an organic radical, selected from the group consisting of phenyl, naphthyl, pyridyl, thiophenyl, furanyl, quinolinyl, thiazolyl, benzothiazolyl, pyrimidyl, $C_{1-10}$-alkyl, $C_{3-10}$-alkenyl and cyclohexyl, said organic radical being unsubstituted or substituted by a group selected from the group consisting of $C_{1-20}$-alkyl, $C_{1-20}$-alkoxy, $C_{2-20}$-alkenyl, $C_{1-20}$-alkylthiol, $C_{1-20}$-alkoxycarbonyl, hydroxy$C_{1-4}$-alkoxy, phenyl, benzyl, phenylthio, fluoro, chloro, bromo, —CN, —NO$_2$, —CF$_3$, —COR$^2$, —COOR$^2$, —CONR$^2$R$^3$, —SO$_2$R$^2$, —SO$_2$NR$^2$R$^3$, NR$^2$R$^3$ and —OR$^2$ in which R$^2$ and R$^3$ are each independently H, $C_{1-4}$-alkyl or phenyl and —SO$_3$A in which A is —H, a metal or an ammonium ion radical and the remaining peripheral carbon atoms are unsubstituted or substituted by a substituent selected from the group consisting of halogen, —SO$_3$A wherein A is H, a metal or an ammonium ion, and an organic radical as defined above, provided that the phthalocyanine absorbs electromagnetic radiation at a wavelength from 650 nm to 800 nm;

(b) compounds of the Formula (2)

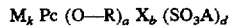  Formula (2)

wherein:

$M_k$pC is a phthalocyanine nucleus as defined in Formula (1);

each R independently is an organic radical selected from the group consisting of phenyl, naphthyl, pyridyl, thiophenyl, furanyl, quinolinyl, thiazolyl, benzothiazolyl, pyrimidyl, $C_{1-10}$-alkyl, $C_{3-10}$-alkenyl and cyclohexyl, said organic radical being unsubstituted or substituted by a group selected from the group consisting of $C_{1-20}$-alkyl, $C_{1-20}$-alkoxy, $C_{2-20}$-alkenyl, $C_{1-20}$-alkylthiol, $C_{1-20}$-alkoxycarbonyl, hydroxy$C_{1-4}$-alkoxy, phenyl, benzyl, phenylthio, fluoro, chloro, bromo, —CN, —NO$_2$, —CF$_3$, —COR$^2$, —COOR$^2$, —CONR$^2$R$^3$, —SO$_2$R$^2$, —SO$_2$NR$^2$R$^3$, NR$^2$R$^3$ and —OR$^2$ in which R$^2$ and R$^3$ are each independently H, $C_{1-4}$-alkyl or phenyl and —SO$_3$A in which A is —H, a metal or an ammonium ion;

each X independently is halogen or hydrogen;

A is selected from H, a metal or ammonium;

a is from 1 to 16;

b is from 0 to 15;

d is an average value from 0.1 to 50;

a+b is from 1 to 16; and (c) compounds of the Formula (3)

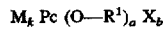  Formula (3)

wherein:

$M_k$Pc is as defined in Formula (1);

R$^1$ is selected from aryl and heteroaryl each of which, independently, is unsubstituted or is substituted by a substituent selected from the group consisting of $C_{1-20}$-alkyl, $C_{1-20}$-alkoxy, $C_{2-20}$-alkenyl, $C_{1-20}$-alkylthiol, $C_{1-20}$-alkoxycarbonyl, hydroxy$C_{1-4}$-alkoxy, phenyl, benzyl, phenylthio, fluoro, chloro, bromo, —CN, —NO$_2$, —CF$_3$, —COR$^2$, —COOR$^2$, —CONR$^2$R$^3$, —SO$_2$R$^2$, —SO$_2$NR$^2$R$^3$, NR$^2$R$^3$ and —OR$^2$ in which R$^2$ and R$^3$ are each independently H, $C_{1-4}$-alkyl or phenyl;

X is halogen or H;

a is an integer from 1 to 16;

b is an integer from 0 to 15; and a+b is equal to 16;

the fabrics being exposed to daylight during or following the treatment.

2. A process according to claim 1, wherein M is selected from the group consisting of H, Zn, ClAl.OHAl, ClRh, OHRh, ClIn, BrIn, OHIn, ClGa, OHGa, Pt, Pd, Li, Na, K, Ca, Ba, Mg, ClSc and OHSc.

3. A process according to claim 2, wherein M is H, Zn, ClAl or OHAl.

4. A process according to claim 1, 2 or 3, wherein said organic radical or R is a phenyl or naphthyl radical.

5. A process according to claim 1, 2, or 3, wherein the compound is of Formula (2) or (3) and b is 0.

6. A process according to claim 5, wherein said organic radical or R is a phenyl or naphthyl radical.

7. A process according to claim 1, 2, or 3, wherein the compound is of Formula (1) or (2) substituted by from 16 to 30 —SO$_3$A groups.

8. A process according to claim 1, 2 or 3, the compound is of Formula (2) or (3), a is 4, 12 or 16, b is 12, 4 or 0 and a+b is equal to 16.

9. A process according to claim 8, wherein the compound is of Formula (1) or (2) substituted by from 16 to 30 —SO$_3$A groups.

* * * * *